Jan. 8, 1963 E. W. ROSS Plant Pat. 2,211
PECAN TREE
Filed May 2, 1961 2 Sheets-Sheet 1
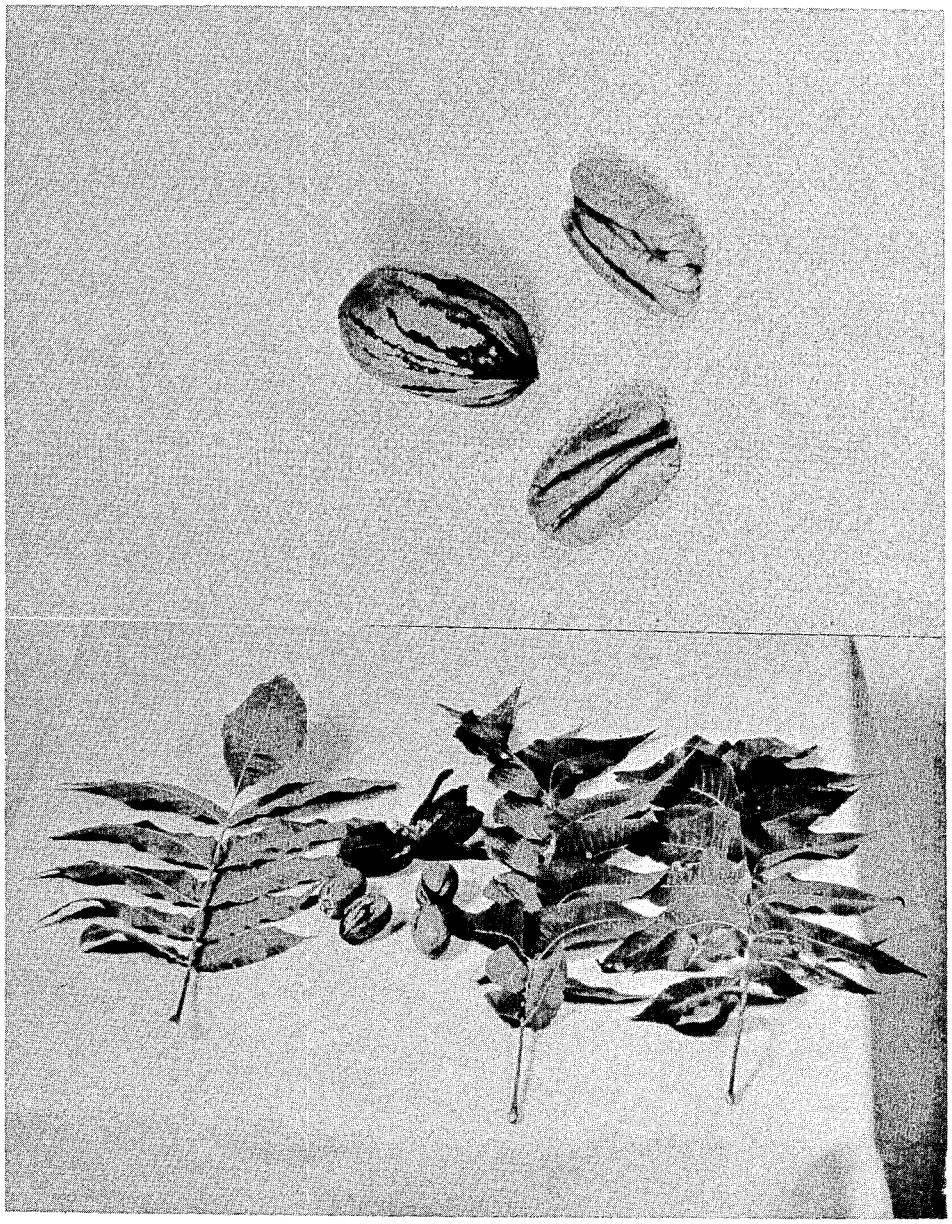
INVENTOR
Earl Wallace Ross
BY Robb & Robb
ATTORNEYS Jan. 8, 1963 E. W. ROSS Plant Pat. 2,211
PECAN TREE
Filed May 2, 1961 2 Sheets-Sheet 2
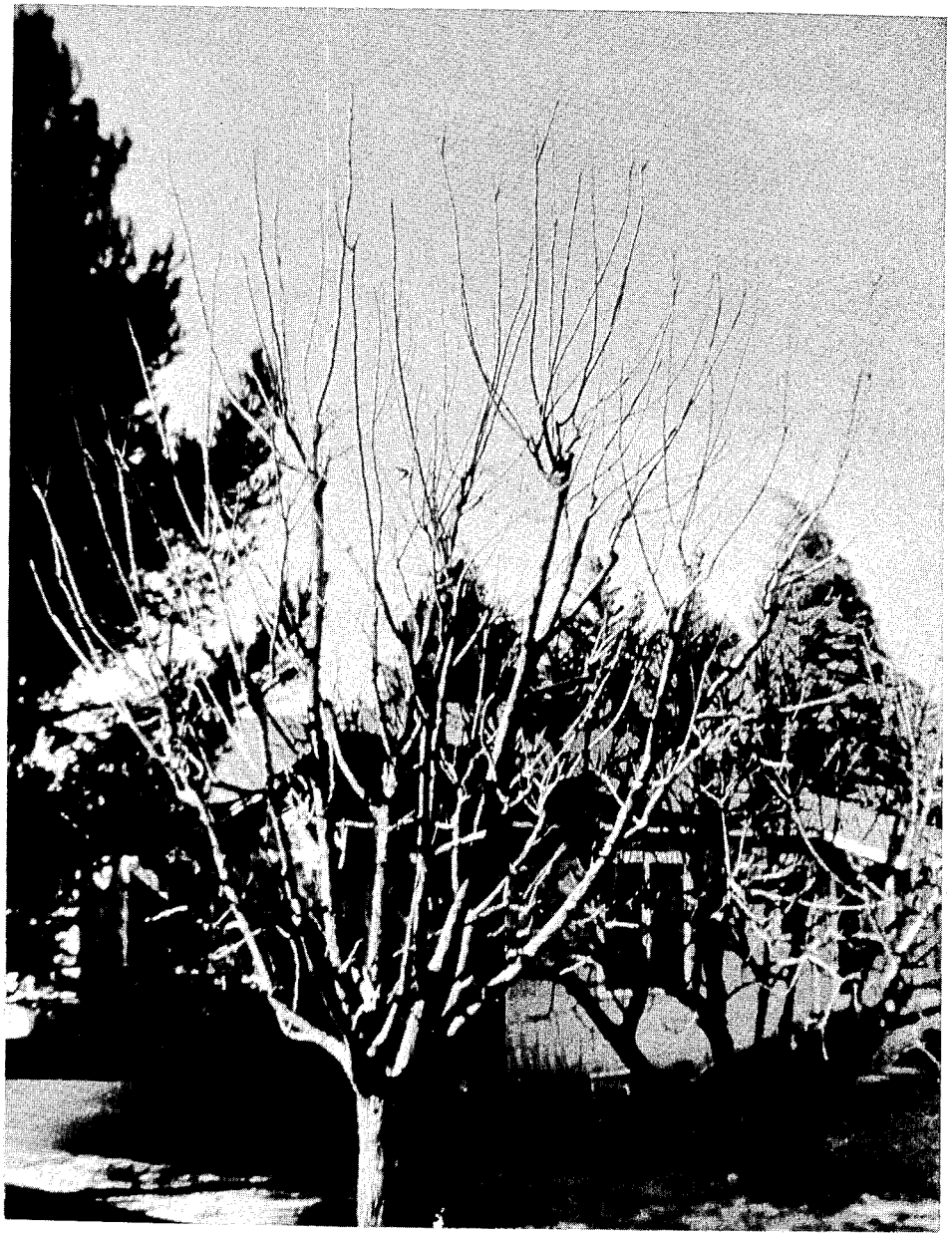
Inventor
Earl Wallace Ross
By: Robb & Robb
Attorneys.

United States Patent Office

Plant Pat. 2,211
Patented Jan. 8, 1963

2,211
PECAN TREE

Earl Wallace Ross, San Antonio, Tex., assignor to R. C. Aldridge, Sr., doing business as Aldridge Nursery, Von Ormy, Tex.

Filed May 2, 1961, Ser. No. 107,275
1 Claim. (Cl. 47—62)

The present invention relates to a new and distinct variety of pecan tree, which originated as a cultivated seedling derived from the planting of seeds of unknown origin and type on cultivated property at San Antonio, Texas.

During the course of growing these seedlings referred to above, which were planted for the purpose of producing understocks on which other standard pecan varieties were to be grafted, I found that one of the seedlings possessed outstanding and unique qualities, which prompted me to carefully preserve this particular seedling and keep it under close observation, instead of using it for understock purposes. The tree was topped back, fertilized and kept watered until its qualities could be more fully evaluated. In due course, asexual reproductions thereof were made, as performed by both budding and grafting at San Antonio, Texas, and these reproductions came true to form and corresponded in all respects to the original seedling.

My observations of the original seedling and the asexually reproduced progeny fully confirmed my initial belief that the new seedling was a new and distinct variety, as evidenced by the following unique combination of characteristics which are outstanding and which distinguish it from all other varieties of which I am aware:

(1) A vigorous habit of growth;
(2) An upright and ascending tree form;
(3) An attractive appearance of both the tree and nuts.
(4) Good bearing qualities;
(5) Large, smooth symmetrical, thin-shelled and well-filled nuts which crack and release from the shell quite easily and shell out a very good kernel percentage; and
(6) A pleasing and sweet flavor of the kernels.

The accompanying drawings show typical specimens of the foliage and nuts of my new variety, with certain of the nut specimens shown as unshelled and other specimens shown as shelled kernels, and one of the drawings showing in the foreground a specimen tree in the dormant stage and in a somewhat pruned-back condition, but clearly depicting the characteristic upright and ascending form of the tree.

The following is a detailed description of the new pecan variety, with color terminology in accordance with Nickerson Color Fan, published by Munsell Color Company, Inc., of Baltimore, Maryland (hereinafter referred to as "Nickerson"), and Dupont Color Chest, depicting Dupont custom colors as currently used by paint dealers and distributors (hereinafter referred to as "Dupont"), except where general color terms of ordinary dictionary significance are obvious, as based upon observations made at San Antonio, Texas:

Tree: Large size; vigorous; rather upright and ascending habit of growth; heavy limbs, with bark of trunk and older limbs acquiring the usual furrowing commonly found in pecan trees as they grow older. Twigs—become very smooth as young shoots mature; color—usually from grayish green to grayish brown, depending on age.

Foliage:

*Leaves.*—Normal abundance; usually from 9 to 19 leaflets per stem.

*Leaflets.*—Short-stalked; slightly serrate; definitely glandular; tomentose when young, but becoming glabrous with maturity. Shape—usually oblong-lanceolate. Size (when mature): length—from 4 to 8 inches; breadth—from 1 to 3 inches. Color—Moderate Yellow Green, Plate 7.5GY 5/7 (Nickerson).

Buds: Medium length; pointed shape. Color—gray-green during growing season, but yellowish-green when dormant.

Flowers: Both pistillate and staminate flowers produced in the usual manner and shape in the early spring.

Nuts:

*Ripening habit.*—Quite uniform.

*Dates of first and last picking.*—About October 10 and about November 1, respectively; nuts generally ripen in late October, but may vary up to two weeks earlier or later according to seasonal weather conditions and other geographical factors.

*Quantity.*—Heavy bearing.

*Cluster.*—Nuts borne in clusters ranging from 2 to 10 in number, but averaging 4 or 5 per cluster.

*Shuck.*—Usually 4-sectioned shuck common to most pecans but slightly heavier or thicker in comparison with common varieties now in cultivation.

*Individual nuts.*—Size—large; length—from 2 to 2½ inches; diameter—from 1 to 1¼ inches. Average number of nuts to pound—28; substantially heavier than nuts of other standard varieties which range in number as follows: "Success" (unpatented)—37; "Western Schley" (unpatented)—59; "Stuart" (unpatented)—55; and "Burkett" (unpatented)—40. Shape—symmetrical; smooth; oblong; rather blunt on the base end and tapering to a point on the opposite end. Shell—medium thin (about 3/64 inch); cracks and releases quite easily; color—rich brown and slightly more tan than Plate 10YR 5/6 (Nickerson), overlaid with irregular markings of from dark brown to black. Kernel—large; plump; fill the shells well; very good kernel percentage averaging about 55% as compared with other leading commercial varieties which have the following averages: "Success"—52%; "Western Schley"—60%; "Stuart"—44%; and "Burkett"—55%. Color—Golden Brown, Color No. 1170 (Dupont), with Creamy-White, Color No. 1166 (Dupont) interior color when broken. Sutures—each half of kernel has 2 regular even sutures that release readily from the shell. Flavor—pleasant; sweet.

I claim:

A new and distinct variety of pecan tree, substantially as herein shown and described, characterized particularly as to novelty by the unique combination of a vigorous habit of growth, an upright and ascending tree form, an attractive appearance of both the tree and nuts, good bearing qualities, large, smooth, symmetrical, thin-shelled and well-filled nuts which crack and release from the shell quite easily and shell out a very good kernel percentage, and a pleasing and sweet flavor of the kernels.

No references cited.